United States Patent
Garibaldi et al.

(10) Patent No.: US 6,375,606 B1
(45) Date of Patent: Apr. 23, 2002

(54) METHODS OF AND APPARATUS FOR TREATING VASCULAR DEFECTS

(75) Inventors: Jeffrey M. Garibaldi, St. Louis; Bevil J. Hogg, Town and Country, both of MO (US); Roger N. Hastings, Maple Grove; Brooke Ren, Champlin, both of MN (US)

(73) Assignee: Stereotaxis, Inc., St. Louis, MO (US)

( * ) Notice: Subject to any disclaimer, the term of this patent is extended or adjusted under 35 U.S.C. 154(b) by 0 days.

(21) Appl. No.: 09/430,118

(22) Filed: Oct. 29, 1999

Related U.S. Application Data

(63) Continuation-in-part of application No. 09/271,118, filed on Mar. 17, 1999.

(51) Int. Cl.⁷ .......................... A61M 37/00; A61N 2/00
(52) U.S. Cl. ........................................................ 600/12
(58) Field of Search ............................. 600/12, 9, 11, 600/585; 606/32, 108, 198; 424/9

(56) References Cited

U.S. PATENT DOCUMENTS

| | | | | |
|---|---|---|---|---|
| 5,353,807 A | * | 10/1994 | DeMarco | 600/585 |
| 5,851,218 A | * | 12/1998 | Lev | 606/198 |
| 5,895,385 A | * | 4/1999 | Gugliemi et al. | 606/32 |
| 5,951,566 A | * | 9/1999 | Lev | 606/108 |
| 6,015,414 A | * | 1/2000 | Werp et al. | 606/108 |

OTHER PUBLICATIONS

Laksne et al, Iron–acrylic Compound for Stereotaxic Aneurysm Thrombosis, J Neurosurgery 47:137–141 (1977).*

* cited by examiner

Primary Examiner—Robert L. Nasser
Assistant Examiner—Brian Szmal
(74) Attorney, Agent, or Firm—Harness, Dickey & Pierce, PLC

(57) ABSTRACT

A method of and apparatus for treating vascular defects. A catheter having a selectively energizeable coil on its distal end. The catheter is particularly adapted for the delivery of magnetic embolic materials. The coil can be energized to aid in the magnetic navigation of the catheter, to help retain magnetic material in the catheter, to draw ejected magnetic material back into the catheter. A catheter can also be used to deliver a magnetic patch that can be magnetically applied to a vascular defect such as an aneurysm.

22 Claims, 5 Drawing Sheets

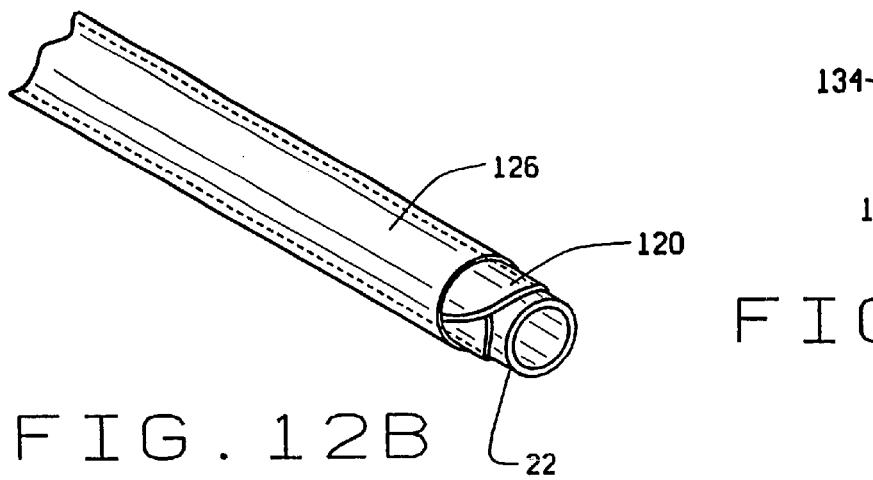
FIG. 12B
FIG. 14
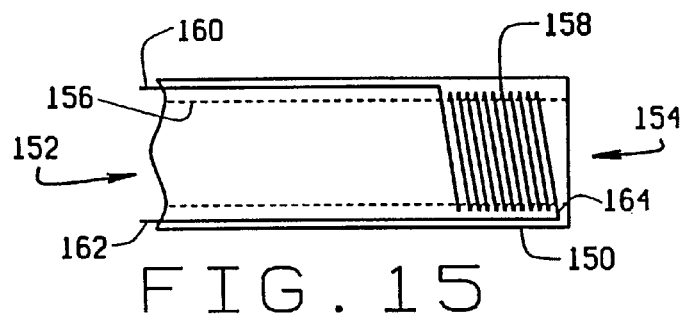
FIG. 15
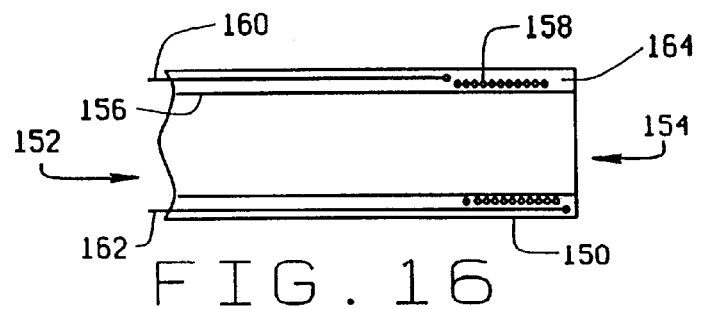
FIG. 16
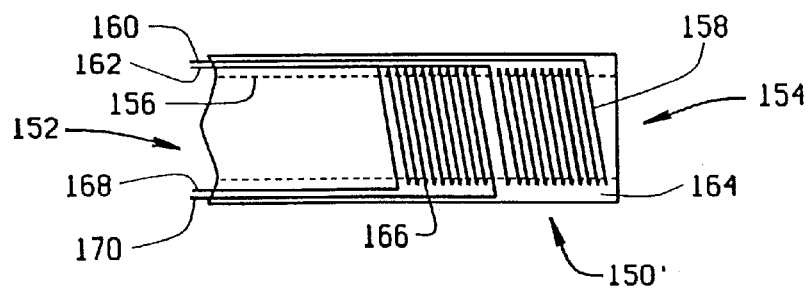
FIG. 17

METHODS OF AND APPARATUS FOR TREATING VASCULAR DEFECTS

CROSS-REFERENCE TO RELATED APPLICATION

This application is a continuation-in-part of prior U.S. patent application Ser. No. 09/271,118, filed Mar. 17, 1999, entitled "Magnetic Vascular Defect Treatment System" incorporated herein by reference.

FIELD OF THE INVENTION

This invention relates to methods of and apparatus for treating vascular defects, such as aneurysms and atriovenous malformations, and in particular a method and related apparatus for treating such defects with magnetically manipulated objects and materials.

BACKGROUND OF THE INVENTION

There are many types of vascular defects that can be treated by blocking the defect. One example of such a defect is an aneurysm, which is a permanent, abnormal blood-filled dilatation or ballooning of a blood vessel that may be congenital or the result of disease. Aneurysms typically have thin walls vulnerable to rupture. If an aneurysm ruptures, the resulting hemorrhage that can put injurious pressure on surrounding tissue, impair downstream blood flow, and even cause death. Another example of a vascular defect is an atriovenous malformation—a typically congenital shunt formed between an artery and a vein that often carries a substantial blood flow. One of the principal complications in treating these and other vascular defects is the blood flow in the adjacent vessels which impairs treatment, but should be maintained for the health of the patient.

Current treatments for aneurysms include embolizing the aneurysm to remove the dilatation or balloon from the wall of the vessel. In the most mature technique, the surgeon accesses the region of the aneurysm under direct visualization and places one or more aneurysm clips on the opening or "neck" of the aneurysm. While this conventional surgical technique has a high rate of success, it is highly invasive and for that reason it is undesirable. More recently, less invasive techniques have been developed for the treatment of aneurysms. One such technique involves the introduction of small wire coils into the aneurysm. A catheter is navigated to the site of the aneurysm, and the coils are delivered through the lumen of the catheter into the aneurysm. The coils reduce the blood flow through the aneurysm, which results in clotting within the aneurysm. This coiling procedure can be time consuming both in navigating the catheter through the vasculature to the site of the aneurysm, and in introducing the coils into the aneurysm. In some cases, the shape of the aneurysm allows the coils to escape from the aneurysm, requiring the coil to be retrieved and replaced.

Another less invasive technique for treating vascular defects is the delivery of embolic materials to the site of the vascular defect to occlude the defect. In the case of an aneurysm a balloon is inflated over the neck of the aneurysm and a liquid embolic agent is introduced into the aneurysm. Attempts have been made to deliver embolic agents directly into the dilation or balloon of the aneurysm. Embolic agents have also been used to occlude atriovenous malformations, but it can be difficult to accurately deliver the embolic agents. In one of the more common procedures a catheter is navigated to the site of the atriovenous malformation and particles of polyvinyl alcohol with sizes selected for the particular application are introduced. This procedure requires guessing at the proper size of the particles and there is limited control over the placement of the particles, which upon release follow the path of greatest flow.

SUMMARY OF THE INVENTION

The present invention provides improved methods and related devices for treating vascular defects. According to one aspect of this invention, various magnetic objects are provided that can be delivered intravascularly through a catheter and which can be guided into and/or held in place in the vascular defect with an applied magnetic field. One embodiment of these magnetic objects includes magnetic coils. These coils may either be magnetic, or include magnetic elements. Another embodiment of these magnetic objects includes a magnetic patch, adapted to cover the vascular defect. The magnetic patch may include a hoop for ensuring that the patch is fully deployed.

In another aspect of this invention, a catheter is provided for delivering the magnetic objects and materials of the present invention. The catheter has a proximal end and a distal end, and lumen therebetween. There is a coil at the distal end, and leads extending along the catheter by which a current can be selectively applied to the coil at the distal end 26 of the catheter. Current can be selectively applied to the coil on the distal end of the catheter to selectively enhance the magnetic responsiveness of the distal end of the catheter so that it can be navigated in the body with an externally applied magnetic field, but the coil can be disconnected from current so that the coil does not interfere with the delivery of magnetic objects or magnetic materials through the lumen. The magnetism created by the current in the coil is enhanced by the presence of the magnetic objects or the magnetic material in the lumen of the catheter. The coil can also be energized to help retain magnetic materials in the lumen of the catheter. A second coil may be provided on the catheter to enhance magnetic responsive and to enhance the ability to retain magnetic materials in the lumen. In another embodiment, lateral coils (as opposed to circumferential coils) are provided in the sidewall of the catheter. These coils facilitate movement of the distal end 26 of the catheter, for example when it is n the opening of an aneurysm.

Thus, the method and devices of the present invention allows a catheter to be brought to the procedure site through magnetically assisted navigation, but the catheter can remain at the site as a further magnetic procedure, such as the magnetic delivery of magnetic objects and magnetic materials, is conducted.

BRIEF DESCRIPTION OF THE DRAWINGS

FIG. 12B is a perspective view of an alternate apparatus for deploying the patch;

FIG. 14 is a cross-sectional view of a magnetic pellet constructed according to the principles of this invention;

FIG. 15 is a side elevation view of a catheter incorporating a coil in the distal end in accordance with the principles of this invention;

FIG. 16 is a longitudinal cross-sectional view of the catheter shown in FIG. 15;

FIG. 17 is a side elevation view of a catheter incorporation two coils in the distal end 26 in accordance with a first alternate embodiment.

Corresponding reference numerals indicate corresponding parts throughout the several views of the drawings.

DETAILED DESCRIPTION OF THE INVENTION

Figure 1:
FIG. 1 is a side elevation view of a first embodiment of a magnetic coil constructed according to the principles of this invention.

A first embodiment of a magnetic coil constructed according to the principles of this invention is indicated generally as 20 in FIG. 1. The magnetic coil 20 is preferably made from a permeable magnetic material, such as 400 series stainless steel of Hiperco™ wire, or some other suitable material. The magnetic coil 20 could also be made from a permanent magnetic material, such as a combination of neodymium iron boron powder in a polymer binder. The magnetic coil 20 preferably has a length of between about 20 mm and about 200 mm, and a diameter of between about 0.010 inches and about 0.018 inches.

Figure 2A:
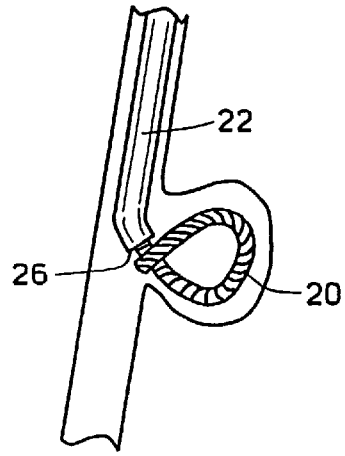
FIG. 2A is a side elevation view of the magnetic coil of the first embodiment shown as it is being inserted in an aneurysm without an externally applied magnetic field.
Figure 2B:
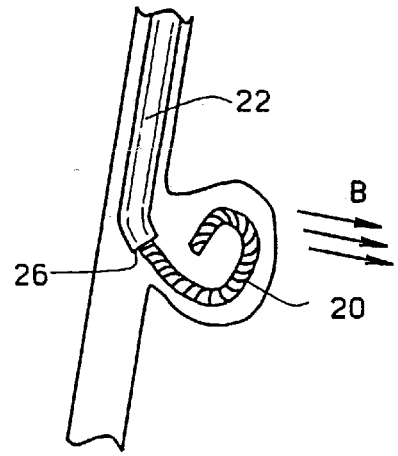
FIG. 2B is a side elevation view of the magnetic coil of the first embodiment shown as it is being inserted in an aneurysm with an externally applied magnetic field in accordance with the present invention.

As shown in FIG. 2, the magnetic coil 20 is delivered to the site of the vascular defect in the patient, in this case an aneurysm, inside a catheter 22. The catheter 22 may be a conventional catheter having a proximal end, a distal end 26, and a lumen extending therebetween. The distal end 26 of the catheter 22 is navigated to the aneurysm, for example using a guide wire. Once at the site of the aneurysm, the coil 20 is then ejected from the distal end 26 of the catheter 22. A magnetic field, as indicated by arrows B, is applied at the site of the aneurysm to draw the coil 20 into the aneurysm. (The magnetic gradient is preferably parallel to the magnetic field). The coil 20 is advanced from the distal end 26 of the catheter 20, and in contrast to when no magnetic field is applied as shown in FIG. 2A, the application of the magnetic field helps keep the coil within the aneurysm as shown in FIG. 2B, so that the coil 20 coils upon itself in the aneurysm. Additional coils 20 may be inserted in the aneurysm until the aneurysm is substantially filled, and blood flow in the aneurysm is reduced. This allows clotting in the aneurysm. Eventually the aneurysm is completely occluded.

Figure 3:
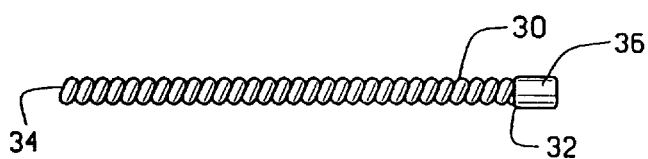
FIG. 3 is a side elevation view of a second embodiment of a coil with a magnetic element constructed according to the principles of this invention.

A second embodiment of a magnetic coil constructed according to the principles of this invention is indicated generally as 30 in FIG. 3. The magnetic coil is preferably made from a nonmagnetic material, such as platinum, or some other suitable material. The magnetic coil 30 preferably has a length of between about 20 mm and about 200 mm, and a diameter of between about 0.010 inches and about 0.018 inches. The magnetic coil 30 has first and second ends 32 and 34. A magnetic element 36 is secured at the first end 32 of the coil 30. The magnetic element 36 can be a magnetically permeable material such as Hiperco™ or cold rolled steel. The magnetic element 36 may also be a permanent magnetic material, such as Neodymium Iron Boron.

Figure 4A:
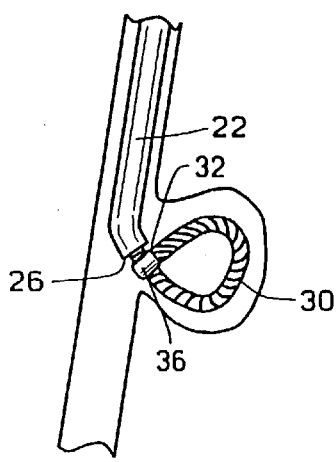
FIG. 4A is a side elevation view of the coil of the second embodiment shown as it is being inserted into an aneurysm without an externally applied magnetic field.
Figure 4B:
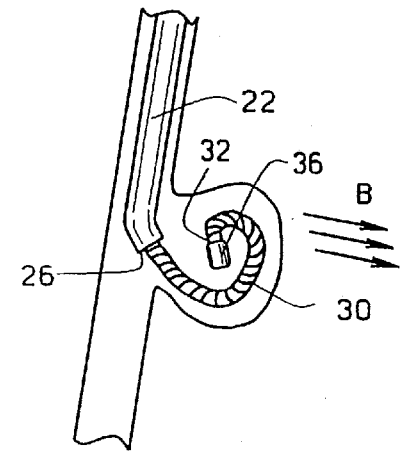
FIG. 4B is a side elevation view of the coil of the second embodiment shown as it is being inserted into an aneurysm with an externally applied magnetic field.

As shown in FIG. 4, the magnetic coil 30 is delivered to the site of the vascular defect in the patient, in this case an aneurysm, inside a catheter 22. Once at the site of the aneurysm, the first end 32 of the coil 30 is ejected from the distal end 26 of the catheter. A magnetic field, indicated by arrows B, is applied at the site of the aneurysm to draw the coil 30 into the aneurysm. (The magnetic gradient is preferably parallel to the magnetic field). The coil 30 is advanced from the distal end 26 of the catheter 22, and in contrast to when no magnetic field is applied as shown in FIG. 4A, the application of the magnetic field helps steer the end of the coil within the aneurysm as shown in FIG. 4B, so that the coil 30 coils upon itself in the aneurysm. Additional coils 30 may be inserted in the aneurysm until the aneurysm is substantially filled, and blood flow in the aneurysm is reduced.

Figure 5:
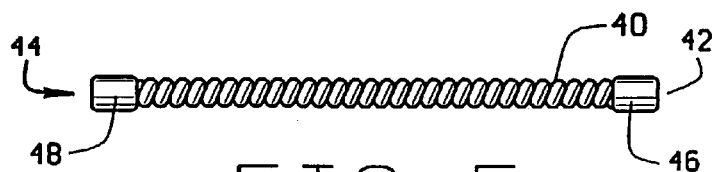
FIG. 5 is a side elevation view of a third embodiment of a coil with two magnetic elements constructed according to the principles of this invention.

A third embodiment of a magnetic coil constructed according to the principles of this invention is indicated generally as 40 in FIG. 5. The magnetic coil 40 is preferably made from a nonmagnetic material, such as platinum, or some other suitable material. The magnetic coil 40 preferably has a length of between about 20mm and about 200 mm, and a diameter of between about 0.010 inches and about 0.018 inches. The magnetic coil 40 has first and second ends 42 and 44. A magnetic element 46 is secured to the first end 42, and a magnetic element 48 is secured to the second end 44. The magnetic elements 46 and 48 can be a magnetic permeable material such as Hiperco™ or cold rolled steel. The magnetic elements 46 and 48 may also be a magnetic material, such as Neodymium Iron Boron. The magnetic elements 46 and 48 allow the coils 40 to be joined end to end in the lumen 28 of the catheter 22. This allows the coils to be delivered into the aneurysm in a continuous strand, if desired.

Figure 6A:
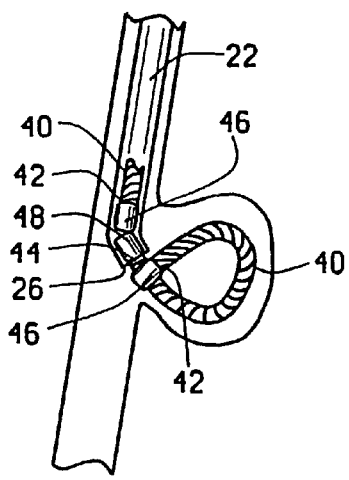
FIG. 6A is a side elevation view of the coil of the third embodiment shown as it is being inserted in an aneurysm without an externally applied magnetic field.
Figure 6B:
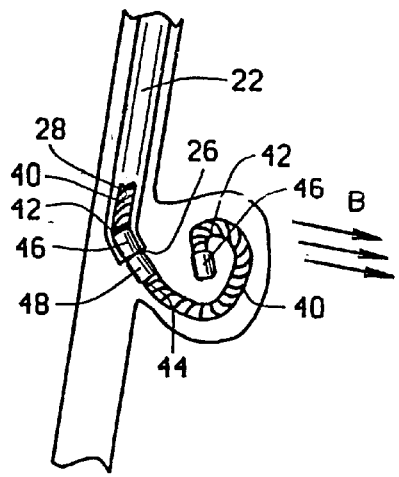
FIG. 6B is a side elevation view of the coil of the third embodiment shown as it is being inserted in an aneurysm with an externally applied magnetic field.

As shown in FIG. 6, a series of magnetic coils 40 is delivered to the site of the vascular defect in the patient, in this case an aneurysm, inside a catheter 22. Once at the site of the aneurysm, the first end 42 of the distal most coil 40 is ejected from the distal end 26 of the catheter 22. A magnetic field indicated by arrows B, is applied at the site of the aneurysm to draw the coil 40 into the aneurysm. (The magnetic gradient is preferably parallel to the magnetic field). The coils 40 are advanced from the distal end 26 of the catheter 22, and in contrast to when no magnetic field is applied as shown in FIG. 6A, the application of the magnetic field helps steer the ends 42 and 49 of the coil 40 within the aneurysm as shown in FIG. 6B, so that the coil 40 coils upon itself in the aneurysm. Additional coils 40 may be inserted in the aneurysm, either as a continuous strand, or separately until the aneurysm is substantially filled, and blood flow in the aneurysm is reduced. Adjacent coils 40 can be separated by changing the direction of the magnetic field or gradient to separate the adjacent coils.

Figure 7:
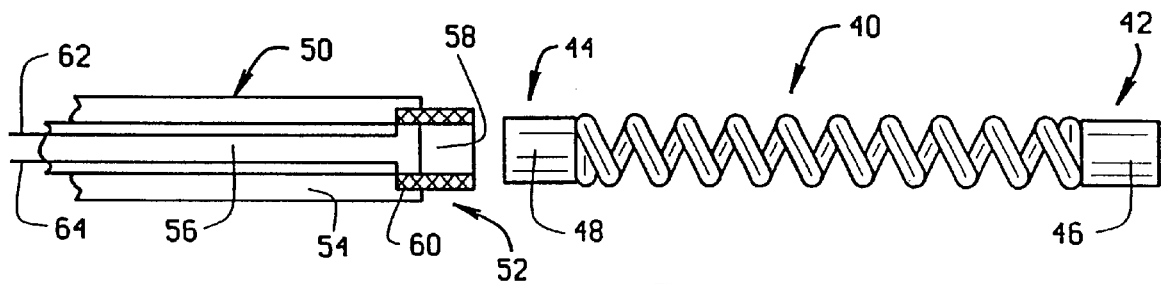
FIG. 7 is a longitudinal cross-sectional view of a catheter and push wire combination adapted for delivery coils in accordance with the principles of the present invention.

The distal end of a catheter 50 for delivering the coil 40 is shown in FIG. 7. The catheter 50 could also be used to deliver coils 20 or 30 or any of the other magnetic objects of the present invention. The catheter 50 has a proximal end, a distal end 52, and a central lumen 54 therein. A push wire 56 is disposed in the lumen 54. The push wire 56 has a magnet 58 on its distal end. The push wire 56 also has a coil 60 on its distal end, generally surrounding the magnet 58. Leads 62 and 64 extend proximally from the coil 60, allowing the coil to be selectively connected to a power supply. The magnet 58 on the distal end of the push wire 56 magnetically engages the magnet 48 on the second end 44 of the coil 40, allowing the push wire 56 to push the coil 40 out of the lumen 54 of the catheter 50. Once the coil 40 has been pushed out of the catheter 50, then the coil 60 can be energized, to neutralize the magnetic attraction between the magnet 58 and the magnet 48 on the second end 44 of the coil 40, to thereby release the coil 40.

Figure 8:
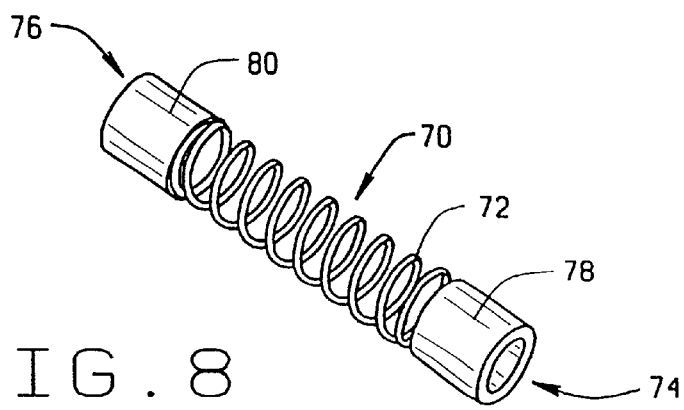
FIG. 8 is a perspective view of a fourth embodiment of a coil constructed according to the principles of this invention.

A fourth embodiment of a coil constructed according to the principles of this invention is indicated generally as 70 in FIG. 8. Coil 70 comprises a coil section 72, and has a having a first end 74 and a second end 76. There is a magnet 78 at the first end 74, and a magnet 80 on the second end 76. The magnets 78 and 80 are preferably tube-shaped.

Figure 9A:
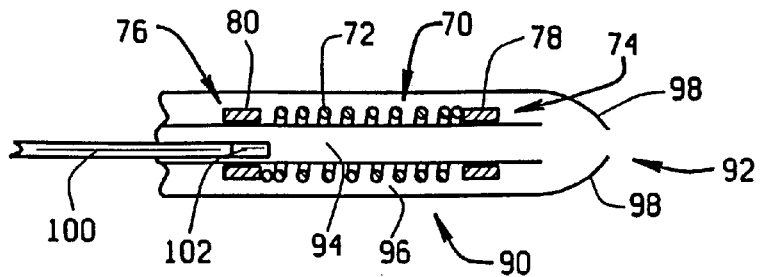
FIG. 9A is a longitudinal cross-sectional view of a catheter adapted for delivering the coil of the fourth embodiment, prior to delivery of the coil.
Figure 9B:
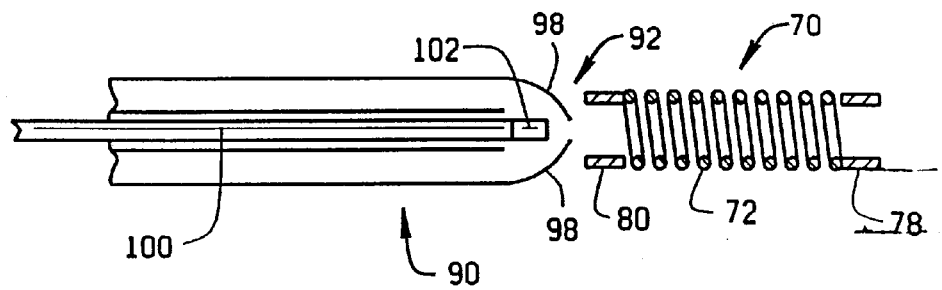
FIG. 9B is a longitudinal cross-sectional view of a catheter adapted for delivering the coil of the fourth embodiment, subsequent to delivery of the coil.

The distal end of a catheter 90 for delivering the coil 70 is shown in FIGS. 9A and 9B. The catheter 90 has a proximal end, a distal end 92. The catheter 90 has a central lumen 94 with a circular cross-section, surrounded by an annular lumen 96. The distal end of the annular lumen 96 is resiliently closed with a flap 98. A push wire 100 having a magnet 102 on its distal end 104, can slide in the central lumen 94. As show in FIG. 9A, the magnet 102 magnetically engages the magnet 80 on the second end 76 of the coil 70. The push wire 100 can be advanced distally in the lumen which pushes the coil 70 distally out of the distal end of the lumen 96. Once the coil 70 has been pushed out of the lumen 96, the flaps 98 close behind it. As shown in FIG. 9B, when the push wire 90 is drawn proximally back into the central lumen 94, the flaps 98 separate the coil 70 from the push wire 100.

Figure 10:
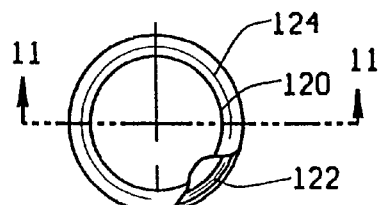
FIG. 10 is a top plan view of a magnetic patch constructed according to the principles of this invention.
Figure 11:
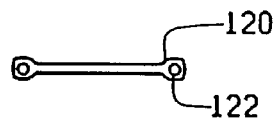
FIG. 11 is a cross-sectional view of a the patch taken along the plane of line 8—8 in FIG. 7.

A magnetic patch 120 constructed according to the principles of this invention is shown in FIGS. 10 and 11. The patch 120 is made from a highly flexible material such as silicone or polyurethane, or some other suitable material. In some embodiments it may be desirable to make the patch from a bioadsorbable material. In the preferred embodiment the patch 120 includes a hoop 122 of nitinol "memory" wire, which allows the patch to be compressed to be delivered through the lumen of a catheter or by being wrapped around the distal end of the catheter. The hoop 122 causes the patch 120 to open to its normal (preferably round) shape. Of course some other structure or construction can be provided to cause the patch to assume its extended configuration. The patch 120 includes magnet material, for example particles of a magnetically responsive material or magnetic wire mesh. The magnetically responsive material may be a permeable magnetic material or it may be a permanent magnetic material. For example food grade iron particles of between about 0.05 $\mu$m and about 50 $\mu$m.

Figure 12A:
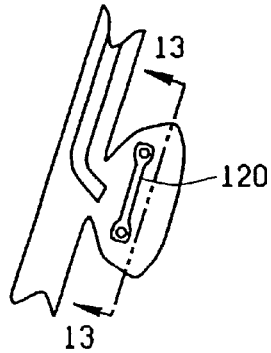
FIG. 12A is a side elevation view of the patch deployed in an aneurysm.
Figure 13:
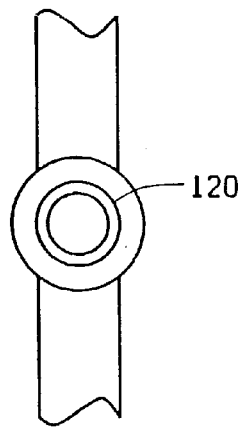
FIG. 13 is a cross-sectional view of the aneurysm, showing the patch occluding the opening of the aneurysm.

As shown in FIG. 12A, the patch is delivered to the interior of the aneurysm. This is conveniently done by navigating the distal end 26 of the catheter 22 into the aneurysm. The patch 120 is then deployed from the lumen of the catheter 22, and the hoop 122 causes the patch 120 to open to its full shape. Alternatively, as shown in FIG. 12B, the patch could be delivered wrapped on the outside of the distal end portion of the catheter 22, and retained thereon by a retractable sheath 126. The catheter 22 is navigated to the site of the vascular defect and the sheath 126 retracted distally to release the patch 120 at the site of the defect. A magnetic field, indicated as arrows B, is then applied to the patch 120 to urge the patch against the interior of the neck of the aneurysm, as shown in FIG. 13. Preferably a transverse magnetic gradient (gradient perpendicular to the field direction) is applied, with the patch 120 being magnetized along a long axis (along its surface) and the transverse gradient pulling the patch parallel to its thickness. The edge margins 124 of the patch 120 preferably have a wettable adhesive thereon, such as a hydrogel, cellulose ether, collagen, or even cyanoacrylate so that the edge margins of the patch adhere to the margins of the interior of the aneurysm surrounding the neck or opening of the aneurysm. Alternatively, the edge margins 124 of the patch 120 may have an adhesive activated by some other agent, such as a chemical agent, ultraviolet light, or laser. Thus the patch 120 covers the opening of the aneurysm. The patch can also have growth promoting substances on its surface, such as Vascular Endothelial Growth Factor (VEGF) promote growth of epithelial cells over the patch to close covered aneurysm opening.

The patch 120 could also be used to cover injured sections on the inside walls of the patient's vasculature. In this use, the patch might contain agents which promote healing and/or tissue growth, such as VEGR and even cells. The patch 120 could be applied to sites of plaque rupture, or to sites of intra-vascular therapy such as angioplasty or atherectomy. A patch 120 can be applied to one side of a blood vessel, while being held in place by a transverse gradient field, or multiple patches could be applied sequentially around the inside circumference of a blood vessel by successive rotating the field gradient direction. In this latter case, the patches would collectively form a continuous interior wall reinforcement, like a stent. This stent could be adsorbable over time by the body, and contain agents which promote healing of the arterial wall.

As shown in FIG. 14 the magnetic object can also be a pellet 130 comprising magnetically responsive particle 132, with a coating 134 of a biocompatible material such as polyvinyl alcohol. The magnetically responsive particle 132 may be iron and preferably has a diameter of between about 1 $\mu$m and about 500 $\mu$m. With the coating 134, the pellet preferably has a diameter of between about 100 $\mu$m and about 1000 $\mu$m. The pellets 130 can be delivered from the lumen of a catheter navigated to the site of the vascular defect. A magnetic field can be applied from an external source magnet to guide the pellets 130 into a particular branch of an atriovenous malformation, and hold them in place to occlude the malformation.

In accordance with the methods of this invention, magnetic fields are used to deploy and place magnetic objects and magnet materials to treat vascular defects. However this means that magnetic navigation techniques generally cannot be used to navigate the delivery catheter, because magnetizing the distal end 26 of the catheter would interfere with the delivery of the magnetic objects. However, in accordance with another aspect of this invention, and as shown in FIGS. 15 and 16, a catheter 150, having a proximal end 152, a distal end 154, and a lumen 156 therebetween, is provided with a coil 158 formed in its distal end 154. Leads 160 and 162 extend along the wall 164 of the catheter to selectively apply an electric current to the distal end 154 of the catheter 150. The application of current to the coil 158 magnetizes the distal end 154 of the catheter 150, allowing it be navigated by the application of a magnetic field with an external source magnet. Thus with current applied to the coil 158 via leads 160 and 162, the distal end 154 of the catheter 150 can be conveniently navigated to the site of the vascular defect by the application of a magnetic field, or with the assistance from an applied magnetic field. While the magnetic objects in the lumen 156 are not sufficiently responsive to allow magnetic navigation of the catheter 150 containing them, magnetic objects or magnetic material in the lumen, together with the energized coil 158, render the catheter sufficiently magnetically responsive so that it can be magnetically navigated or at least navigated with magnetic assistance. The coil 158 may be 5 mm (0.200 inch) long, and comprises 5 layers, each layer having 200 turns of AWG 50 insulated copper or silver magnet wire. The magnetic material in the lumen will typically have a $\mu$ ranging from about 10 to about 100. For a magnetic material with a $\mu$ of 25, a current of 0.2 A will achieve a magnetization of 1 T, which is comparable to permanent magnets used in magnetic navigation. With a current of 0.5 A, a magnetic material in the lumen having a $\mu$ of 10 will achieve a similar level of magnetization. Currents as high as 0.5 A in this coil should not significantly raise the local temperature, provided there is adequate blood flow for cooling.

The coil 158 in catheter 150 also facilitates the delivery of magnetic materials, such as magnetic embolic agents. The coil 158 can be energized to help retain the magnetic embolic material in the catheter 150 as the catheter is navigated to and navigated from the site of the vascular defect, functioning as a valve.

An alternative construction of catheter 150 indicated as 150' is shown in FIG. 17. Catheter 150', in addition to having coil 158, also has coil 166, with leads 168 and 170 extending along wall 164. The coil 166 can be connected in series with coil 158 to enhance the magnetic effect at the distal tip of the catheter 150'. The coil 166 can also be connected oppositely from coil 158, so that together the coils cut off the flow of magnetic embolic material through the lumen 156 of the catheter 150', but the net magnetic effect distal to the catheter is negligible so that the catheter 150' does not disturb the magnetic embolic agent that has already been deposited.

Figure 18:
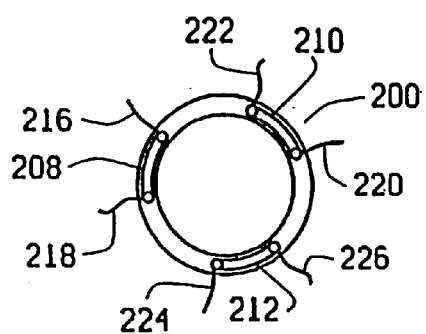
FIG. 18 is a transverse cross-sectional view of a catheter incorporating three coils in the distal end in accordance with a second alternative embodiment.
Figure 19:
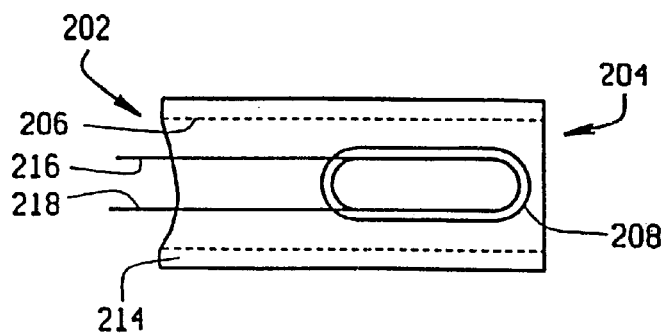
FIG. 19 is a side elevation view of the second alternative embodiment of a catheter.
Figure 20:
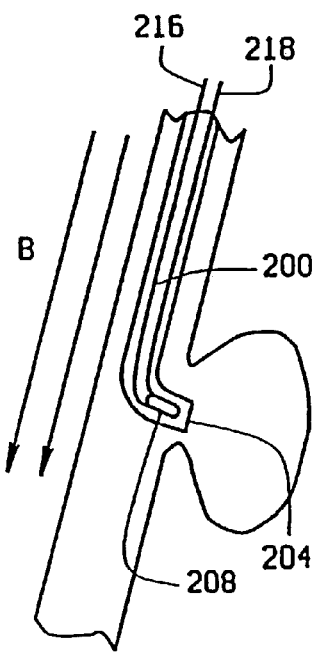
FIG. 20 is a side elevation view of the second alternative embodiment of the catheter shown as it could be positioned in the neck of an aneurysm.

As shown in FIGS. 18 and 19, a catheter 200, having a proximal end 202, a distal end 204, and a lumen 206 therebetween, is provided with three coils 208, 210, and 212 formed in its distal end 204. The sidewall 214 of the catheter 200 contains leads 216 and 218 extending to coil 208, leads 220 and 222 extending to coil 210, and leads 224 and 226 extending to coil 212. The leads allow the coils 208, 210 and 212 to be selectively energized. The coils 208, 210, and 212 can be energized to facilitate magnetic navigation of the distal end 204 of the catheter 200 to the vascular defect. The coils can also be selectively energized at the site of the vascular defect to manipulate the distal end 204 of the catheter 200 to control the delivery of a magnetic embolic agent. For example, as shown in FIG. 20, if the catheter 200 has been navigated to an aneurysm and is being used to deliver a magnetic embolic agent into the dilatation or balloon of the catheter, the tip of the catheter would be pointing into the neck of the aneurysm, and the applied magnetic field would be preferably oriented transversely to the neck of the aneurysm, with the gradient oriented toward the back wall of the aneurysm, to deposit the magnetic embolic agent in layers in the aneurysm. Selectively energizing one or more of the coils 208, 210, and 212 allows the position of the distal end 204 of the catheter 200 to be adjusted.

The catheters 150 and 150' of the present invention also permit ejected magnetic material to be drawn into the lumen of the catheter. By properly energizing the coil 158, magnetic material can be magnetically drawn into the lumen even when the viscosity of the magnetic material and small lumen size would make it difficult or impossible to suction the material back into the lumen. With the catheter 200' of the present invention, the coils 158 and 166 can be differentially energized to apply a force to draw in magnetic material immediately adjacent the distal end of the catheter, and to repel magnetic material more than a few millimeters away. This prevents the catheter from drawing a string of material from the mass of ejected material or otherwise disturbing the mass of ejected material.

Figure 21A:
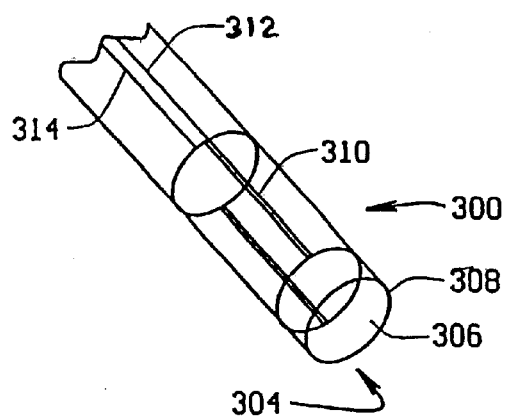
FIG. 21A is a perspective view of a catheter constructed according to the principles of this invention.
Figure 21B:
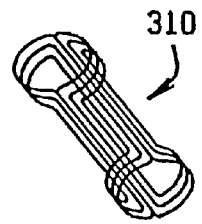
FIG. 21B is a perspective view of the split rectangular coil incorporated into the catheter of FIG. 21A.

A catheter 300 having a proximal end, a distal end 304, and a lumen 306 therebetween is shown in FIG. 21A. The wall 308 of the catheter 300 has a coil 310 embedded therein. As shown in FIG. 21B, the coil 310 is a split longitudinal coil. Leads 312 and 314 extend longitudinally in the wall 308 to the proximal end of the catheter 300 to permit the coil to be selectively connected to a power supply. Catheter 300, like catheter 200 can be manipulated within an applied magnetic field by selectively applying power to the coil 310.

An important aspect of this invention is the ability to visually monitor the treatment process. A preferred method is the use of bi-planar fluoroscopy to provide images of the treatment site in the patient. In bi-planar imaging two images of the treatment site are provided from different angles (preferably 90° apart). Real time imaging has generally not been available in prior magnetic treatment procedures because the magnetic fields interfered with the operation of the imaging equipment. However, the inventors have discovered that by using shielded x-ray sources and digital imaging plates such as LAST plates, available from Varian Medical Systems, Inc., real time imaging can be provided in the presence of the relatively strong magnetic fields (which typically range from about 0.01 T to 0.5 T at the treatment site) for the magnetic treatment procedures of the present invention.

Bi-planar imaging also provides a convenient interface for physician control of the procedure. By computer processing and display of the images, the displays can be used by the physician to identify the current positions of the treatment devices and the desired future positions and orientations of the treatment devices. For example, the user can manipulate a cursor or other indicator on the display with a mouse, joystick, or other input device and "click" at the points to identify a particular point. By identifying a point on each of the two bi-planar displays the point is uniquely identified in three dimensional space. The computer can then determine and implement the necessary movements of the external source magnet to achieve the desired future positions and orientations.

The physician can also identify desired field and/or gradient directions on the displays, and the computer can then determine and implement the necessary movements of the external source magnet or electrical current changes in an electromagnet to achieve the desired field and/or gradient directions.

OPERATION

In operation, a magnetic object for treating a vascular defect is delivered by navigating the distal end of a catheter to the site of the vascular defect. The magnetic object may or may not already be in the distal portion of the lumen of the catheter during this navigation. In the case of a coil 20, 30, or 40, the coil is preferably at least partly ejected from the distal end 204 of the catheter and a magnetic field applied from an external source magnet. The field is preferably aligned in the direction of the opening of the aneurysm, and the gradient is preferably toward the back wall of the aneurysm.

In the case of the magnetic coil 20, as the coil is advanced, as shown in FIG. 28 the applied magnetic field compresses the coil, pulling it toward the back wall of the aneurysm, and away from the open neck of the aneurysm. As more of the coil 20 is advanced into the aneurysm. The applied magnetic field prevents the end of the coil from snaking out the open neck, and allows the coil to be wound inside the aneurysm to substantially occlude the aneurysm. Additional coils 20 can be delivered in this manner until the aneurysm is satisfactorily occluded.

In the case of the coil 30 with magnetic elements on at least one end, as the coil is advanced, as shown in FIG. 4B the applied magnetic field steers the magnetic element 36 on the first end 22 of the coil toward the back wall of the aneurysm, and away from the open neck of the aneurysm. The applied magnetic field prevents the first end 32 of the coil 30 from snaking out the open neck, and allows the coil to be wound inside the aneurysm to substantially occlude the aneurysm. Additional coils 30 can be delivered in this manner until the aneurysm is satisfactorily occluded.

In the case of the coil 40 with magnetic elements on each end, as the coil is advanced as shown in FIG. 6B, the applied magnetic field steers the magnetic elements 46 and 48 on the ends 42 and 44 of the coil toward the back wall of the aneurysm, and away from the open neck of the aneurysm. This prevents the ends of the coil from snaking out the open neck, and allows the coil to be wound inside the aneurysm to substantially occlude the aneurysm. The coils 40 can be inserted continuously end to end, or each coil can be separately introduced. The coils can be separated at the distal end of the catheter 22 by turning the magnetic field to torque the magnetic element 48 on the proximal end 44 of the distal most coil 40 from the magnetic element 46 on the distal end 42 of the adjacent coil. A continuous strand of several coils 40, or several separate coils 40, can be inserted until the aneurysm is satisfactorily occluded.

In the case of a magnetic patch 50, the catheter 22 is navigated to the neck of the aneurysm, and the patch is introduced into the aneurysm. The resilient hoop 52 causes the patch to expand to its normal flat configuration. The blood present in the aneurysm wets the adhesive on the edge margins 54 of the patch 50. A magnetic field is applied to the aneurysm to urge the patch 50 against the opening of the aneurysm. The magnetic field helps to hold the patch 50 in place until the patch is secured, occluding the opening of the aneurysm.

In the case of the magnetic pellets 60, the catheter 22 is navigated to the site of the vascular defect and the pellets are released from the distal end 26 of the catheter. A magnetic field is applied to the vascular defect, in a direction of the branch to be occluded. The pellets 60 align in the direction of the applied magnetic field and travel in the direction of the applied gradient to occlude the vascular defect.

In the case of a magnetic embolic agent, the catheter is navigated to the site of the vascular defect. A magnetic field is applied and the magnetic embolic agent is ejected from the distal end of the catheter. The magnetic field rigidfies the ejected magnetic embolic agent. Thus, the magnetic field can be applied to rigidify the magnetic embolic agent and hold its shape until the magnetic embolic agent hardens on its own. A long rigid plug can be extruded from the catheter for occluding an atriovenous malformation. The applied magnetic field rigidifies and helps the plug retain its shape as the plug is advanced into the atriovenous malformation.

What is claimed:

1. A catheter adapted for magnetic guidance inside the body, the catheter having a proximal end, a distal end, and a lumen therebetween, a magnetic material in the lumen adjacent the distal end and adapted for ejection from the distal end; a coil on the distal end, and leads extending along catheter to the coil for applying a current to the coil to magnetize the distal end of the catheter to increase the responsiveness to an externally applied magnetic field.

2. A catheter adapted for magnetic guidance inside the body, the catheter having a proximal end, a distal end, and a lumen therebetween, a magnetic material in the lumen adjacent the distal end and adapted for ejection from the distal end; a coil on the distal end, and leads extending along catheter to the coil for selectively applying a current to the coil to selectively block the ejection of magnetic material from the distal end of the catheter.

3. The catheter according to claim 2 wherein the magnetic material includes a permanent magnetic material.

4. A method of treating a vascular defect comprising:

navigating the distal end of a catheter having a lumen therein with a magnetic embolic material in the lumen, and a coil associated with the distal end, to the site of the vascular defect while maintaining a current on the coil to retain the magnetic embolic material in the lumen;

ejecting the magnetic embolic material from the lumen of the catheter and guiding with an externally applied magnetic field to form an embolus that occludes the vascular defect;

withdrawing the distal end of the catheter while maintaining a current on the coil to retain the magnetic embolic material in the lumen.

5. The method according to claim 4 wherein the magnetic embolic material contains a permanent magnetic material.

6. The method according to claim 4 wherein the magnetic embolic material contains a permeable magnetic material.

7. A method of treating a vascular defect comprising:

navigating the distal end of a catheter having a lumen therein with a magnetic embolic material in the lumen, and a coil associated with the distal end, to the site of the vascular defect by applying a current to the coil to create a magnetic moment at the distal end of the catheter and using an externally applied magnetic field to orient the distal end of the catheter;

ejecting the magnetic embolic material from the lumen of the catheter, and applying a magnetic field to guide the ejected material to form an embolus that occludes the defect.

8. The method according to claim 7 wherein the current to the coil is reduced before ejecting magnetic embolic material from the lumen.

9. The method according to claim 7 wherein the magnetic field to guide the ejected material is applied before the material is ejected.

10. The method according to claim 7 wherein a magnetic field of a first direction is applied and material is ejected from the lumen and wherein thereafter a magnetic field of a second direction is applied and additional material is ejected from the lumen.

11. The method according to claim 7 wherein gradient of the magnetic field at the site of the vascular defect is perpendicular to the direction of the magnetic field.

12. The method according to claim 7 wherein the gradient of the magnetic field at the site of the vascular defect is parallel to the direction of the magnetic field.

13. The method according to claim 7 wherein the intensity of the magnetic field is reduced as the magnetic embolic material is ejected.

14. A method of treating a vascular defect comprising:

navigating the distal end of a catheter having a lumen therein with a magnetic embolic material in the lumen, and a coil associated with the distal end, to the site of the vascular defect;

ejecting the magnetic embolic material from the lumen of the catheter and guiding with an externally applied magnetic field to form an embolus that occludes the vascular defect;

applying a current to the coil to selectively draw excess ejected magnetic embolic material back into catheter.

15. A method of treating a vascular defect, comprising:

navigating the distal end of a catheter having a lumen to the site of the vascular defect;

deploying a magnetic patch from the distal end of the catheter;

applying a magnetic field to the deployed patch to urge the patch against the vascular defect.

16. The method according to claim 15 wherein the patch comprises a flexible sheet material, and a resilient hoop which extends the flexible sheet material.

17. A method of treating an aneurysm defect, comprising:

navigating the distal end of a catheter having a lumen into the aneurysm;

deploying a magnetic patch from the distal end of the catheter into the aneurysm;

applying a magnetic field to the deployed patch to urge the patch against the opening of the aneurysm to close the aneurysm.

18. The method according to claim 17 wherein the patch comprises a flexible sheet material, and a resilient hoop which extends the flexible sheet material.

19. A method of treating an aneurysm, the method comprising:

navigating the distal end of a catheter through the vasculature and into the aneurysm;

deploying a magnetic patch from the distal end of the catheter into the aneurysm;

applying a magnetic field to the aneurysm to urge the magnetic patch against the opening of the aneurysm.

20. The method of treating an aneurysm according to claim 19 wherein the patch comprises a flexible sheet material, and a resilient hoop which extends the flexible sheet material.

21. A method of treating an aneurysm that opens to a blood vessel through a neck, the method comprising:

navigating the distal end of a catheter through the vasculature and into the neck of the aneurysm;

ejecting a coil, having a proximal end and a distal end and a magnet on the distal end, through the distal end of the catheter by pushing the coil with a guide inside the lumen of the catheter, the guide having a magnet on its distal end for magnetically engaging the magnet on the proximal end of the coil;

applying a magnetic force to the juncture between the coil and the guide to break the magnetic engagement between the coil and the guide, and release the coil into the aneurysm.

22. A method of treating an aneurysm that opens to a blood vessel through a neck, the method comprising:

navigating the distal end of a catheter through the vasculature and into the neck of the aneurysm; the catheter having a first coil, having a proximal end and a distal end and a magnet on the distal end, at least one intermediate coil, each intermediate coil having a proximal end and a distal end, and a magnet on each end; the magnets on adjacent ends of adjacent coils magnetically engaging each other, and the guide having a magnet on its distal end for magnetically engaging the magnet on the proximal end of the most proximal intermediate coil;

ejecting the first coil and at least one intermediate coil from the distal end of catheter;

applying a magnetic force to the juncture with the ejected coils to break the magnetic engagement between the coil and the guide, and release the coil into the aneurysm.

* * * * *